United States Patent
Van De Craen et al.

(10) Patent No.: US 10,878,957 B2
(45) Date of Patent: Dec. 29, 2020

(54) NEED DETERMINATION SYSTEM

(71) Applicant: KONINKLIJKE PHILIPS N.V., Eindhoven (NL)

(72) Inventors: Dieter Maria Alfons Van De Craen, Balen (BE); Benjamin Lopez Lopez, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 613 days.

(21) Appl. No.: 15/193,150

(22) Filed: Jun. 27, 2016

(65) Prior Publication Data
US 2017/0004270 A1 Jan. 5, 2017

(30) Foreign Application Priority Data
Jun. 30, 2015 (EP) .................... 15174614

(51) Int. Cl.
| | |
|---|---|
| G16H 40/63 | (2018.01) |
| G06N 20/00 | (2019.01) |
| G06Q 10/06 | (2012.01) |
| G06Q 50/22 | (2018.01) |
| G06Q 10/10 | (2012.01) |

(52) U.S. Cl.
CPC ............. *G16H 40/63* (2018.01); *G06N 20/00* (2019.01); *G06Q 10/06315* (2013.01); *G06Q 10/105* (2013.01); *G06Q 50/22* (2013.01); *A61B 2505/07* (2013.01)

(58) Field of Classification Search
CPC combination set(s) only.
See application file for complete search history.

(56) References Cited

U.S. PATENT DOCUMENTS 7,945,458 B1 * 5/2011 Jackson ................ G06Q 10/10
 705/2
2004/0034286 A1 2/2004 Kasper et al.
(Continued)

FOREIGN PATENT DOCUMENTS

KR 100799665 B1 * 1/2008
KR 20100021894 A * 2/2010

OTHER PUBLICATIONS

Romani, Maya & Ashkar, Khalil, Burnout among physicians, Feb. 17, 2014, Libyan Journal for Medicine (Year: 2014).*
Ling, Tok Wang, Database Schema Design Using Entity-Relationship Approach, Oct. 30, 2014, National University of Singapore (Year: 2014).*
(Continued)

*Primary Examiner* — Aryan E Weisenfeld
*Assistant Examiner* — Karen A Hranek

(57) ABSTRACT

The invention relates to a need determination system including a user interface for enabling a person to input a current combination of a current subject, at least one current informal caregiver (ICG) giving care to the current subject, and at least one relationship between the current subject and the at least one current ICG. A combination similarity measure is applied to the current combination and stored combinations, in order to determine a stored combination which is similar to the current combination, where a need of the current subject and/or a need of the at least one current ICG are determined based on one or more needs assigned to a stored subject and/or stored ICGs of the determined similar stored combination. This allows for a reliable and fast determination of needs of a subject and/or an ICG with relatively low technical efforts.

17 Claims, 4 Drawing Sheets

(56) References Cited

U.S. PATENT DOCUMENTS

| | | | | |
|---|---|---|---|---|
| 2005/0076060 | A1* | 4/2005 | Finn | G06Q 20/201 |
| 2010/0088095 | A1* | 4/2010 | John | G10L 15/22 |
| | | | | 704/235 |
| 2011/0137670 | A1* | 6/2011 | Utterback | G06Q 10/06 |
| | | | | 705/2 |
| 2012/0166206 | A1* | 6/2012 | Feely | G06Q 10/10 |
| | | | | 705/1.1 |
| 2013/0035946 | A1* | 2/2013 | Ratan | G06F 19/3418 |
| | | | | 705/2 |
| 2013/0231953 | A1* | 9/2013 | Ebadollahi | G06F 19/00 |
| | | | | 705/3 |
| 2014/0214441 | A1* | 7/2014 | Young | G16H 10/20 |
| | | | | 705/2 |
| 2014/0358570 | A1 | 12/2014 | Tesanovic et al. | |
| 2015/0088540 | A1* | 3/2015 | Lo | A61B 5/742 |
| | | | | 705/2 |
| 2016/0162992 | A1* | 6/2016 | England | G06Q 40/06 |
| | | | | 705/36 R |
| 2018/0068407 | A1* | 3/2018 | Sicard | G16H 50/30 |

OTHER PUBLICATIONS

Amershi et al., Power to the people: the role of humans in interactive machine learning, 2014, AI Magazine, 35(4), 105-120 (Year: 2014).*

Feinberg, Lynn & Houser, Ari, Assessing Family Caregiver Needs: Policy and Practice Considerations, Jun. 2012, AARP Public Policy Institute (Year: 2012).*

Assessing Family Caregivers: A Guide for Health Care Providers, 2008, Next Step in Care (Year: 2008).*

L. Feinberg & A. Houser, Assessing Family Caregiver Needs: Policy and Practice Considerations, 2012, AARP Public Policy Institute (Year: 2012).*

Aloulou et al: "Deployment of Assistive Living Technology in a Nursing Home Environment: Methods and Lessons Learned"; BMC Medical Informatics and Decision Making; 2013, vol. 13:42, pp. 1-17.

Lavdaniti et al: "In-Hospital Informal Caregivers' Needs as Perceived by Themselves and by the Nursing Staff in Northern Greece: A Descriptive Study"; BMC Nursing, 2011, vol. 10:19, pp. 1-8.

Kiani: "Combined Structure-Weight Graph Similarity and Its Application in E-Health"; Proceedings of the 4th Canadian Semantic Web Symposium, (CSWS 2013), 8 Page Document.

* cited by examiner

NEED DETERMINATION SYSTEM

CROSS-REFERENCE TO PRIOR APPLICATIONS

This application claims the benefit or priority of EP Application No. 15174614.6 filed on Jun. 30, 2015, which is incorporated herein in whole by reference.

FIELD OF THE INVENTION

The invention relates to a need determination system and method for determining at least one need of a subject and/or at least one need of at least one informal care giver (ICGs) who gives care to the subject. The invention further relates to a user interface for being used by the need determination system and a computer program for controlling the need determination system.

BACKGROUND OF THE INVENTION

Subjects who suffer from one or more long term conditions often need a combination of different services, in order to address their needs. These needs can be physical, but also mental and/or social. The subjects are typically surrounded by ICGs who are persons in the environment of the person like a spouse, children, neighbors, friends, et cetera. The ICGs take up active roles in the care process of the subject and have particular challenges. It is important to also address these challenges, in order to improve the life of the ICGs and hence of the subject. However, the challenges of the ICGs are often not taken into account when defining a combination of different services for improving the condition of the subject.

Assessing the needs of a subject is typically done through face-to-face interaction between a health care provider like a health coach in the US or a community matron in the UK, the subject and the ICGs. However, identifying all needs of the subject and of the ICGs is cumbersome and often difficult to accomplish. This identification of the needs is important, because it forms the basis on which a combination of different services will be determined. Without a reliable determination of these needs, only a sub-optimal combination of different services may be defined.

The article "In-hospital informal caregivers' needs as perceived by themselves and by the nursing staff in Northern Greece: A descriptive study" by Maria Lavdaniti et al., BMC Nursing, 10:19 (2011) discloses a study comparing the perceptions of nurses and of ICGs about the ICGs knowledge and informational needs, as well as the factors that influence these perceptions. However, it is not disclosed how the needs of the subject and of the ICGs can reliably and fast be determined with relatively low technical efforts.

SUMMARY OF THE INVENTION

It is an object of the present invention to provide a need determination system and method which allow for a reliable and fast determination of at least one need of a subject and/or of at least one need of at least one ICG, who gives care to the subject, with relatively low technical efforts. In other words, the present invention enables care provider, such as ICG to collect a more complete set of needs for the subject in a significantly shorter timeframe which enables the adequate assessment of the at least one need of a subject and/or of at least one need of at least one ICG, thereby improving care efficiency as well as care outcome(s) within a subject-ICG interaction.

In a first aspect of the present invention a need determination system is presented, wherein the need determination system comprises:

a user interface for allowing a person to input a current combination of a current subject, at least one current ICG giving care to the current subject, and at least one relationship between the current subject and the at least one current ICG, a stored combinations providing unit for providing stored combinations of a stored subject, at least one stored ICG and at least one relationship between the stored subject and the at least one stored ICG, wherein a respective stored combination further includes at least one need assigned to the respective stored subject and/or at least one need assigned to the respective at least one stored ICG of the respective stored combination, a similarity unit for applying a combination similarity measure to the current combination and the stored combinations, in order to determine a stored combination which is similar to the current combination, a need determination unit for determining at least one need of the current subject based on the at least one need assigned to the stored subject of the determined similar stored combination and/or at least one need of the at least one current ICG based on the at least one need assigned to the at least one stored ICG of the determined similar stored combination.

By applying a combination similarity measure to the current combination and the stored combinations, in order to determine a stored combination which is similar to the current combination, and by determining at least one need of the current subject based on the at least one need assigned to the stored subject of the determined similar stored combination and/or at least one need of the at least one current ICG based on the at least one need assigned to the at least one stored ICG of the determined similar stored combination, the at least one need of the current subject and/or the at least one need of the at least one current ICG can be reliably and fast determined with relatively low technical efforts.

The combination of the current subject, the at least one current ICG and the at least one relationship between the current subject and the at least one current ICG can be regarded as forming a pattern defining the "environment" of the current subject. Preferentially, the user interface comprises a graphical user interface allowing the person to input the current combination. In an embodiment the user interface is adapted to allow the person to a) input a need and assign the input need to the current subject or the at least one current ICG and/or b) confirm or remove a determined need. This inclusion of an interaction with the person for modifying a determined need can further improve the reliability of a finally provided need.

The current combination includes at least one relationship between the current subject and the at least one current ICG, which means that, if the current combination includes only a single ICG, there is only a single relationship between the subject and the ICG, and, if the current combination includes several ICGs, between each pairing subject/ICG a relationship is given.

An ICG is a person in the environment of the subject, who gives care to the subject, like a spouse, children, neighbors, friends, et cetera. An ICG is preferentially not a member of a health organization, has initially preferentially no formal training for giving care to the subject and is preferentially not accountable to standards of conduct of practice. For a preferred definition of the term "informal caregiver" reference is made also to the "Lexicon of Commonly Used Terms" of Canadian Hospice Palliative Care Association.

Needs of the subject are, for instance, bathing, feeding, meals on wheels service, transportation, medication assistance, legal support, financial support, et cetera. Moreover, needs of an ICG are, for instance, training for correctly and efficiently caring for the subject, information about social security, information about health and social care provisions, housekeeping assistance in order to give the respective ICG time for caring for the current subject, et cetera.

The need determination unit can be adapted to determine several needs and to refine the determined needs by using a machine learning algorithm. The input into the machine learning algorithm is the set of needs determined by the need determination unit and the output of the machine learning algorithm is a refined set of needs, wherein in the refined set of needs a) needs, which had been determined by the need determination unit, may have been deleted and/or b) needs, which had not been determined by the need determination unit, may have been added. The machine learning algorithm may be trained by using historical data comprising for different cases, i.e. for different subjects and their ICGs, needs, which had been determined by the need determination unit, and finally confirmed needs, wherein for training the machine learning algorithm the respective set of needs determined for the respective case by the need determination unit forms the respective input and the respective set of confirmed needs for the respective case forms the respective output. The machine learning algorithm can be further trained by using the needs determined by the need determination unit for the current combination of a current subject, at least one current ICG and at least one relationship between the current subject and the at least one current ICG and based on the needs, which have finally been confirmed by the user. By refining the determined set of needs by the using the machine learning algorithm the reliability of the determined needs can be further improved.

In an embodiment the similarity unit is adapted to determine several similar stored combinations, wherein the need determination unit is adapted to determine the at least one need of the current subject based on the at least one need assigned to the stored subjects of the similar stored combinations and/or to determine the at least one need of the at least current ICG based on the at least one need assigned to the stored at least one ICG of the similar stored combinations. In particular, the similar combination determination unit can be adapted to order the stored combinations with respect to the degree of similarity, wherein two or more of the stored combinations, for which the highest degrees of similarity have been determined, may be used for determining the at least one need, i.e., for instance, the needs assigned to the stored subject and stored ICGs of these most similar stored combinations may be determined as the needs of the current subject and the at least one current ICG of the current combination.

The need determination system may further comprise an audio recording providing unit for providing an audio recording of a conversation with the current subject and/or the at least one current ICG and an assignments providing unit for providing assignments between a) needs of a subject and/or an ICG and b) keywords, wherein the need determination unit is adapted to extract keywords from the audio recording and to determine at least one need of the current subject and/or at least one need of the at least one current ICG based on the extracted keywords and the provided assignments between a) needs of a subject and/or an ICG and b) keywords. By also using an audio recording, which may be a pure audio recording or which may be a video recording that includes the audio recording, the determination of the at least one need of the current subject and/or of the at least one need of the at least one current ICG can be further improved.

The audio recording providing unit, the assignments providing unit and the need determination unit can be adapted to determine the at least one need of the current subject and/or the at least one need of the at least one current ICG based on the extracted keywords and the provided assignments between a) needs of a subject and/or an ICG and b) keywords "on the fly". Thus, during a conversation the audio recording providing unit can record the conversation and provide the recorded conversation, i.e. the audio recording, in order to allow the need determination unit to determine a need based on the provided audio recording. However, it is also possible that the audio recording is firstly stored only and later provided to the need determination unit for determining one or several needs.

In an embodiment the need determination system comprises a subject data set providing unit for providing a current subject data set of the current subject comprising subject key data elements, and an assignments providing unit for providing assignments between a) needs of a subject and b) subject key data elements, wherein the need determination unit is adapted to extract a subject key data element from the current subject data set and to determine a need of the current subject based on the extracted subject key data element and the provided assignments between a) needs of a subject and b) subject key data elements. The subject data set comprises, for instance, subject data pertaining to psycho-social, psychological, social, mental clinical, current resource utilizations etcetera of said subject, which can be crucial for determining self-care needs.

Moreover, in an embodiment the need determination system may further comprise an ICG data set providing unit for providing at least one current ICG data set of the at least one current ICG of the current combination, wherein the at least one current ICG data set comprises ICG key data elements, and an assignments providing unit for providing assignments between a) needs of an ICG and b) ICG key data elements, wherein the need determination unit is adapted to extract an ICG key data element from the at least one current ICG data set and to determine a need of the at least one current ICG based on the extracted ICG key data element and the provided assignments between a) needs of an ICG and b) ICG key data elements. The ICG data comprises, for instance, ICG data pertaining to psycho-social, psychological, social, mental clinical, current resource utilizations etcetera of said ICG, which can be crucial for determining care needs.

Furthermore, in an embodiment the need determination system comprises a subject data set providing unit for providing a current subject data set of the current subject, and an assignments providing unit for providing stored subject data sets and assignments between a) needs of a subject and b) the stored subject data sets, wherein the similarity unit is adapted to apply a subject data similarity measure to the current subject data set and the stored subject data sets, in order to determine a stored subject data set being similar to the current subject data set, wherein the need determination unit is adapted to determine a need assigned to the similar stored subject data set as a need of the current subject. Moreover, in an embodiment the need determination system further comprises an ICG data set providing unit for providing at least one current ICG data set of the at least one current ICG of the current combination, and an assignments providing unit for providing stored ICG data sets and assignments between a) needs of an ICG and b) the stored ICG data sets, wherein the similarity unit is adapted to apply an ICG data similarity measure to the at least one current ICG data set and the stored ICG data sets, in order to determine at least one stored ICG data set being similar to the at least one current ICG data set, wherein the need determination unit is adapted to determine a need assigned to the similar at least one stored ICG data set as a need of the at least one current ICG. Considering the subject data set and/or the ICG data set can further improve the quality of the determination of the at least one need of the current subject and/or of the at least one need of the current ICG.

Thus, a subject key data element and/or an ICG key data element may be extracted from a current subject data set and/or a current ICG data set, respectively, wherein the extracted subject key data element and/or the extracted ICG key data element may be used together with corresponding assignments for determining at least one need of the current subject and/or at least one need of the current ICG. Alternatively or in addition, a current subject data set and/or a current ICG data set may be compared with stored subject data sets and/or stored ICG data sets, respectively, in order to determine a similar stored subject data set and/or a similar stored ICG data set, wherein at least one need assigned to the similar stored subject data set and/or at least one need assigned to the similar stored ICG data set, respectively, are determined as at least one need of the current subject and/or at least one need of the current ICG, respectively. The respective current data set used for determining a need based on a key data element and the respective current data set used for determining a need based on finding a similar stored data set may be the same or different. In particular, for the key data element based determination of a need a current data set may be used, which is larger than a current data set used for determining a need based on finding a similar stored data set. The smaller current data set may be regarded as being a subject profile or an ICG profile, respectively, wherein the profile may only include a few characteristics of the current subject or a current ICG, respectively, like age, gender, medical condition, living condition, et cetera. The larger current data set can comprise additional data like doctor notes.

The current and stored combinations may also be regarded as groups, wherein a group includes a subject, at least one ICG and at least one relationship. The combinations or groups may also be provided as graphs. In a preferred embodiment the stored combinations providing unit is adapted to provide the stored combinations as stored graphs, wherein a stored graph comprises nodes, to which the stored subject, the at least one stored ICG and needs are assigned, and at least one edge, which connects the stored subject with the at least one stored ICG and to which the respective at least one relationship between the stored subject and the at least one stored ICG is assigned, wherein the similarity unit is adapted to generate a current graph based on the input current combination and to apply the combination similarity measure to the current graph and the stored graph, in order to determine a stored combination which is similar to the current combination.

In an embodiment the user interface is adapted to allow the person to input the current combination such that it also includes at least one distance between the stored subject and the at least one stored ICG, wherein the stored combinations providing unit is adapted to provide the stored combinations such that they comprise distances between the respective stored subject and the respective stored at least one ICG. If the combinations are represented as graphs with nodes and edges, the distances can be assigned to the edges. For instance, the user interface may be a graphical user interface, wherein the person may place a respective current ICG with a certain distance to the current subject on the graphical user interface, in order to input the certain distance. The person may input the distance depending on an assumed importance of the current ICG for supporting the current subject, i.e., for instance, a current ICG having a larger importance for supporting the current subject may be placed with a shorter distance to the current subject than a current ICG having a smaller importance. Considering the distances between the current subject and the respective current ICG can further improve the quality of determining the needs of the current subject and the current ICGs.

In an embodiment the stored combinations providing unit is adapted to store the current combination and the at least one need assigned to the current subject and/or the at least one need assigned to the at least one current ICG of the current combination, in order to allow the stored combinations providing unit to provide the current combination as a stored combination, while determining at least one need of subject and/or at least one need of at least one ICG for a subsequent combination of a subject, at least one ICG and at least one relationship between the subject and the at least one ICG which will be input via the user interface. Thus, in an embodiment the determined needs, particularly the confirmed determined needs and not the removed determined needs, optionally together with needs directly input by the user, can be used together with the current combination for updating a database comprising the stored combinations and the needs assigned to the stored combinations.

The need determination system preferentially also comprises an output unit for outputting the determined at least one need. The output unit may be a display. It may be integrated with an input unit, for instance, by using a touch sensitive display. In an embodiment the graphical user interface may also show the determined at least one need, i.e. also the graphical user interface may be regarded as being the output unit. Moreover, the output unit can also be adapted to acoustically output the at least one determined need.

In an aspect of the present invention a user interface for being used by the need determination system as defined in claim 1 is presented, wherein the user interface is adapted to allow a person to input a current combination of a current subject, at least one current ICG for giving care to the current subject, and at least one current relationship between the current subject and the at least one current ICG.

In a further aspect of the present invention a needs determination method is presented, wherein the needs determination method comprises:

allowing a person to input a current combination of a current subject, at least one current ICG giving care to the current subject, and at least one relationship between the current subject and the at least one current ICG by a user interface, providing stored combinations of a stored subject, at least one stored ICG giving care to the stored subject and at least one relationship between the stored subject and the at least one stored ICG by a stored combinations providing unit, wherein a respective stored combination further includes at least one need assigned to the respective stored subject and/or at least one need assigned to the respective at least one stored ICG of the respective stored combination, applying a combination similarity measure to the current combination and the stored combinations by a similarity unit, in order to determine a stored combination which is similar to the current combination, determining at least one need of the current subject based on the at least one need assigned to the stored subject of the determined similar stored combination and/or at least one need of the at least one current ICG based on the at least one need assigned to the at least one stored ICG of the determined similar stored combination by a need determination unit.

It shall be understood that the need determination system of claim 1, the user interface of claim 13, the needs determination method of claim 14, and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
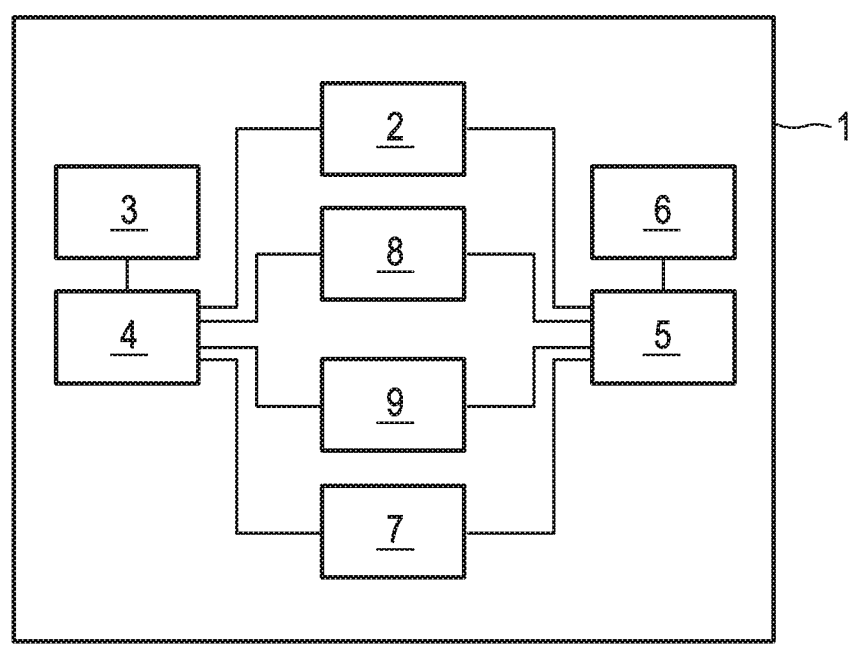
FIG. 1 shows schematically and exemplarily an embodiment of a need determination system for determining needs of a current subject and of current ICGs giving care to the current subject.

FIG. 1 shows schematically and exemplarily an embodiment of a need determination system for determining needs of a subject and of ICGs giving care to the subject. The need determination system 1 comprises a graphical user interface 2 for allowing a person to input a current combination of a current subject, current ICGs and relationships between the current subject and the current ICGs. An embodiment of the graphical user interface 2 is schematically and exemplarily illustrated in FIG. 2. In this example the graphical user interface 2 provides a representation 20 of the current subject surrounded by concentric circles 23. By pressing the button 24 the person can add a stakeholder, i.e. a current ICG in the present case. The graphical user interface 2 then allows the person to name the current ICG to be added and to position the current ICG relative to the representation 20 of the current subject, wherein, while positioning the current ICG with a desired distance to the representation 20 of the current subject, the person may be guided by the concentric circles 23. In the situation exemplarily illustrated in FIG. 2, the person has added a first current ICG named "ICG X" and represented by a representation 21 and a second current ICG named "ICG Y" and represented by a representation 22. The graphical user interface 2 is also adapted to allow the person to add the relationship between the first current ICG and the current subject and between the second current ICG and the current subject. The relationship between the current subject and the respective current ICG is, for instance, spouse, child, brother or sister, friend, et cetera. For instance, the graphical user interface 2 may be adapted to allow the user to press on a certain ICG representation, whereupon a text or menu field may appear, which allows the user to input the relationship, or a corresponding text or menu field may be shown immediately after a current ICG has been added, in order to allow the user to input the relationship. Moreover, the graphical user interface 2 is adapted to allow the person to directly input a need into the need determination system 1 and to assign the input need to the current subject or a current ICG. The process of inputting a need and assigning the need to the current subject or to a current ICG is initiated by pushing the button 25. In the situation schematically and exemplarily shown in FIG. 2 needs 28 have been added and assigned to the current subject, a need 29 has been added and assigned to the first current ICG named "ICG X" and a need 30 has been added and assigned to the current ICG named "ICG Y".

The current combination of the current subject, the current ICGs, the relationships between the current subject and the current ICGs, and also of the distances between the current subject and the current ICGs is regarded as forming a current pattern which can be represented by a current graph. The current graph comprises nodes, to which the current subject and the current ICGs are assigned, and edges, which connect the node, to which the current subject has been assigned, and the nodes, to which the current ICGs have been assigned. The respective distance between the current subject and the respective current ICG and the respective relationship between the current subject and the respective current ICG are assigned to the respective edge. Also the needs already assigned to the current subject and the current ICGs can be assigned to the nodes.

Figure 2:
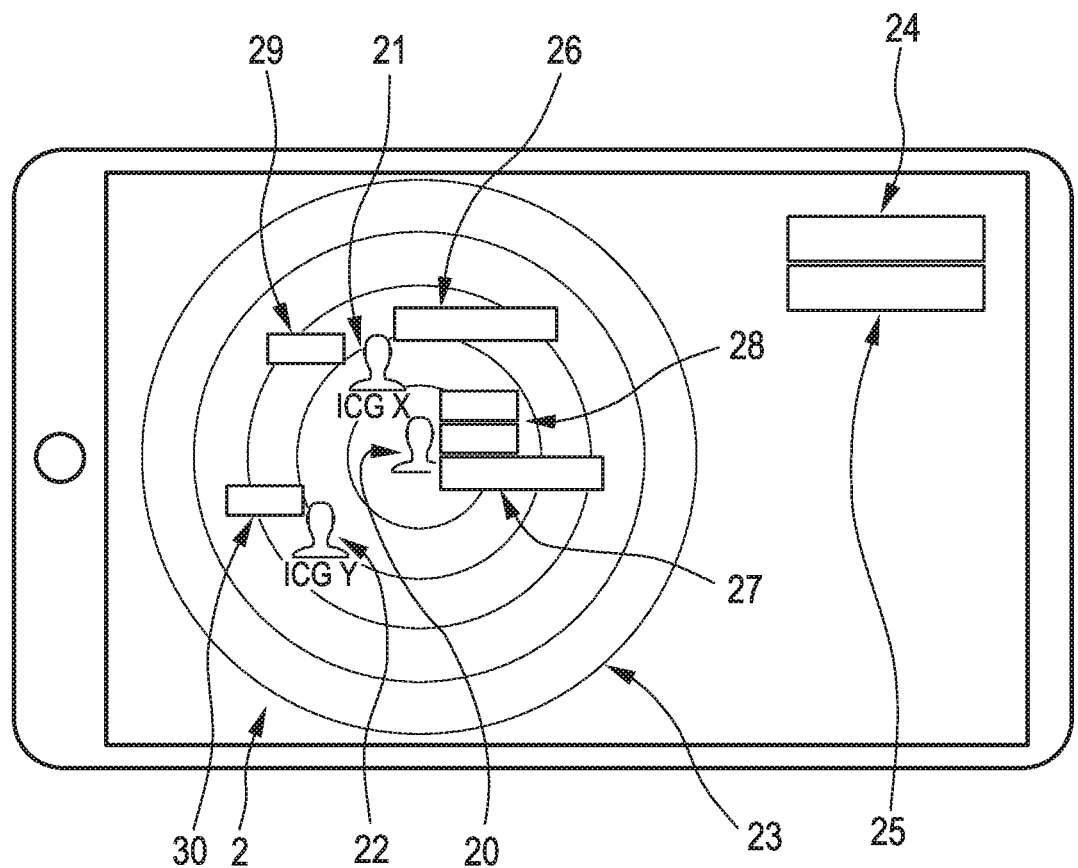
FIG. 2 shows schematically and exemplarily an embodiment of a graphical user interface of the need determination system, FIG. 3 exemplarily illustrates a current graph comprising nodes and edges.
Figure 3:
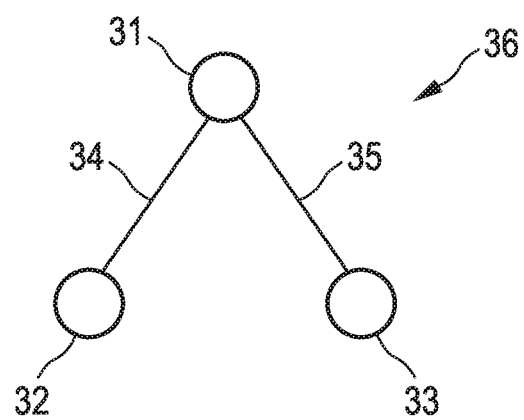

FIG. 3 schematically and exemplarily illustrates a current graph 36 for the situation exemplarily shown on the graphical user interface 2 in FIG. 2. The current graph 36 comprises a subject node 31 to which the current subject has been assigned and to which also the needs 28 can be assigned, wherein the subject node 31 is connected with a first ICG node 32, to which the first current ICG has been assigned and to which also the need 29 can be assigned, and to a second ICG node 33, to which the second current ICG has been assigned and to which also the need 30 can be assigned, via the respective edges 34, 35 to which the respective distances and relationships are assigned.

The need determination system 1 further comprises a stored combinations providing unit 3 for providing stored combinations of a stored subject, stored ICGs and relationships between the stored subject and the stored ICGs. The stored combinations also include needs assigned to the respective stored subject and the respective stored ICGs of the respective stored combination and distances between the respective stored subject and the respective stored ICGs of the respective stored combination. The stored combinations form stored patterns represented by stored graphs, wherein a stored graph comprises nodes, to which the stored subject, the stored ICGs and the corresponding needs are assigned, and edges, which connect a node assigned to a stored subject with a respective node assigned to a stored ICG and to which the respective relationship and distance is assigned. The stored patterns can be historical patterns, i.e. they can be patterns which have been determined for other subjects and their ICGs in the past.

The need determination system 1 further comprises a similarity unit 4 for applying a combination similarity measure to the current combination and the stored combinations, in order to determine a stored combination which is similar to the current combination. In this embodiment the similarity unit 4 is adapted to apply the combination similarity measure to the current graph and the stored graphs, in order to determine a stored graph which is similar to the current graph. The similarity unit 4 can be adapted to use known similarity measures for comparing combinations of parameters, especially for comparing graphs with nodes and edges connecting the nodes, wherein the parameters are assigned to the nodes and edges. For instance, the similarity measure disclosed in the article "Combined Structure-Weight Graph Similarity and its Application in E-Health" by M. Kiani et al., Proceedings of the 4th Canadian Semantic Web Symposium, CEUR Workshop Proceedings, volume 1054, ISSN 1613-0073 (2013) may be used, which is herewith incorporated by reference. The need determination system 1 also comprises a need determination unit 5 for determining needs of the current subject and the current ICGs of the current combination based on the needs assigned to the stored subject and the stored ICGs of the determined similar stored combination.

The similarity unit 4 may determine only a single similar stored combination, i.e. the most similar stored combination, wherein the need determination unit 5 may determine the needs assigned to the stored subject and the stored ICGs of the determined most similar stored combination as the needs of the current subject and the current ICGs of the current combination. These determined needs may be regarded as being possible needs which may be indicated on the graphical user interface 2 by boxes 26, 27 shown in FIG. 2. The person can then confirm or remove the respective possible need 26, 27 by using the graphical user interface 2. If a possible need 26, 27 has been confirmed, it becomes a final need and it is shown on the graphical user interface 2 in the same way, i.e., for instance, with the same color, as the needs 28, 29, 30 directly input by the person into the need determination system 1. The graphical user interface 2 may also be adapted to allow the person to move a possible need from a stakeholder, i.e. a current subject or a current ICG, to another stakeholder and to confirm the need, after it has been moved to the other stakeholder.

The similarity unit 4 can also be adapted to determine several similar stored combinations, wherein the need determination unit 5 can be adapted to determine the needs based on the needs assigned to the stored subject and the stored ICGs of the similar stored combinations. In particular, the similarity unit 4 can be adapted to order the stored combinations with respect to the degree of similarity with the current combination, wherein two or more of the stored combinations, which are at the top of the list, i.e. which have a relatively high degree of similarity, can be used for determining the needs, i.e. the needs assigned to the stored subject and the stored ICGs of these combinations having a relatively high degree of similarity may be determined as the needs of the current subject and the current ICGs of the current combination. Also these determined needs may be regarded as being possible needs which are shown to the person via the graphical user interface 2, wherein the person can confirm or remove these possible needs. Moreover, the person can move a possible need assigned to a certain stakeholder to another stakeholder and confirm the moved need for the other stakeholder.

The need determination system 1 further comprises an audio recording providing unit 6 for providing an audio recording of a conversation with the current subject and/or the current ICGs. The audio recording may be a pure audio recording or it may be a video recording which also includes an audio recording. The need determination system 1 also comprises an assignments providing unit 7 for providing assignments between a) needs of a subject and/or of ICGs and b) keywords extractable from the provided audio recording. The need determination unit 5 is adapted to extract keywords from the audio recording and to determine needs of the current subject and/or of the current ICGs of the current combination based on the extracted key words and the provided assignments between a) needs of a subject and/or of ICGs and b) keywords. For instance, a keyword might be "wheelchair" and the assigned need might be "transportation", or a keyword might be "underfed" and the assigned need might be "meals on wheels". Also these determined needs may be regarded as being possible needs which may be shown on the graphical user interface 2, wherein the person may confirm or remove these possible needs by using the graphical user interface 2. Moreover, also these possible needs may be moved from one of the stakeholders to another of the stakeholders and may be confirmed for the other stakeholder. For extracting keywords from the audio recording known keyword detection algorithms can be used.

The need determination system 1 further comprises a subject data set providing unit 8 for providing a current subject data set comprising subject key data elements, wherein the assignments providing unit 7 is adapted to provide assignments also between a) needs of a subject and b) subject key data elements. The need determination unit 5 is adapted to extract a subject key data element from the subject data set and to determine a need of the current subject based on the extracted subject key data element and the provided assignments between a) needs of a subject and b) subject key data elements. Furthermore, the assignments providing unit 7 is adapted to provide stored subject data sets, which may be regarded as being historical subject data sets, and assignments between a) needs of a subject and b) the stored subject data sets. The similarity unit 4 can be adapted to apply a subject data similarity measure to the current subject data set and the stored subject data sets, in order to determine a stored subject data set being similar to the current subject data set, wherein the need determination unit 5 can be adapted to determine a need assigned to the similar stored subject data set as a need of the current subject. Also the needs, which can be determined based on the subject key data elements and/or based on similarities between the current subject data set and the stored subject data sets can be regarded as being possible needs, which can be shown to the person by using the graphical user interface 2, wherein the person can confirm or remove these possible needs by using the graphical user interface 2. Moreover, also in this case a possible need can be moved from one of the stakeholders to another of the stakeholders and the moved possible need can be confirmed for the other of the stakeholders to which the possible need has been moved.

The need determination system 1 further comprises an ICG data set providing unit 9 for providing a current ICG data set of a current ICG, wherein the current ICG data set comprises ICG key data elements. The assignments providing unit 7 can be adapted to provide assignments also between a) needs of an ICG and b) ICG key data elements, wherein the need determination unit 5 can be adapted to extract an ICG key data element from the current ICG data set and to determine a need of the current ICG based on the extracted ICG key data element and the provided assignments between a) needs of an ICG and b) ICG key data elements. Furthermore, the assignments providing unit 7 can be adapted to provide stored ICG data sets and assignments also between a) needs of an ICG and b) the stored ICG data sets. The similarity unit 4 may be adapted to apply an ICG data similarity measure to the current ICG data set and the stored ICG data sets, in order to determine a stored ICG data set being similar to the current ICG data set, wherein the need determination unit 5 can be adapted to determine a need assigned to the similar stored ICG data set as a need of the current ICG. Also this need is regarded as a possible need, which is shown on the graphical user interface 2 and which can be confirmed or removed by the person. Moreover, also this possible need can be moved from the current ICG to another current ICG or to the current subject by using the graphical user interface 2, wherein the moved possible need may be confirmed by the person via the graphical user interface 2 for the stakeholder to which the possible need has been moved.

The subject data set providing unit may be adapted to provide different current subject data sets a) for extracting subject key data elements and b) for comparing the current subject data set with the stored subject data sets. In particular, the current subject data set used for extracting subject key data elements can be larger than the current subject data set used for finding a similar stored subject data set. For instance, the current subject data set used for finding a similar stored subject data set may be a subject profile comprising only a few characteristics like gender, age, medical condition, living condition, et cetera. The current subject data set used for extracting key data elements can be larger and also include, for instance, doctor notes. The current subject data set used for extracting subject key data elements can be an entire subject file, whereas the current subject data set used for finding similar stored subject data sets can comprise only some data of the complete subject file like the above mentioned gender, age, medical condition, living condition, et cetera. Correspondingly, also the current ICG data set used for extracting ICG key data elements can be larger than the current ICG data set used for finding a similar stored ICG data set. The smaller ICG data set may be an ICG profile only comprising few characteristics like gender, age, medical condition, living condition, et cetera of the respective current ICG. For comparing a current data set with a stored data set known data set similarity measures can be used.

The stored combinations providing unit 3 is preferentially adapted to store the current combination and the needs finally assigned to the current subject and the current ICGs of the current combination, in order to allow the stored combinations providing unit 3 to provide the current combination as stored combination, i.e. as a historic pattern, while determining needs for a subsequent combination of a subject, ICGs, relationships and optionally also distances between the subject and the ICGs, which will be input via the graphical user interface 2 for another, next subject. In this way a database used for determining the needs can grow.

The need determination unit 5 can be adapted to refine the determined needs by using a machine learning algorithm. The input into the machine learning algorithm is the set of needs determined by the need determination unit 5 and the output of the machine learning algorithm is a refined set of needs, wherein in the refined set of needs a) needs, which had been determined by the need determination unit 5, may have been deleted and/or b) needs, which had not been determined by the need determination unit 5, may have been added. The machine learning algorithm may be trained by using historical data comprising for different cases, i.e. for different subjects and their ICGs, the needs, which had been determined by the need determination unit 5, and the finally confirmed determined needs, wherein for training the machine learning algorithm the respective set of needs determined for the respective case by the need determination unit 5 forms the respective input and the respective set of confirmed determined needs for the respective case forms the respective output. The machine learning algorithm can be further trained by using the needs determined by the need determination unit 5 for the current combination of a current subject, current ICGs and relationships between the current subject and the current ICGs and based on the determined needs, which have finally been confirmed by the user.

Figure 4:
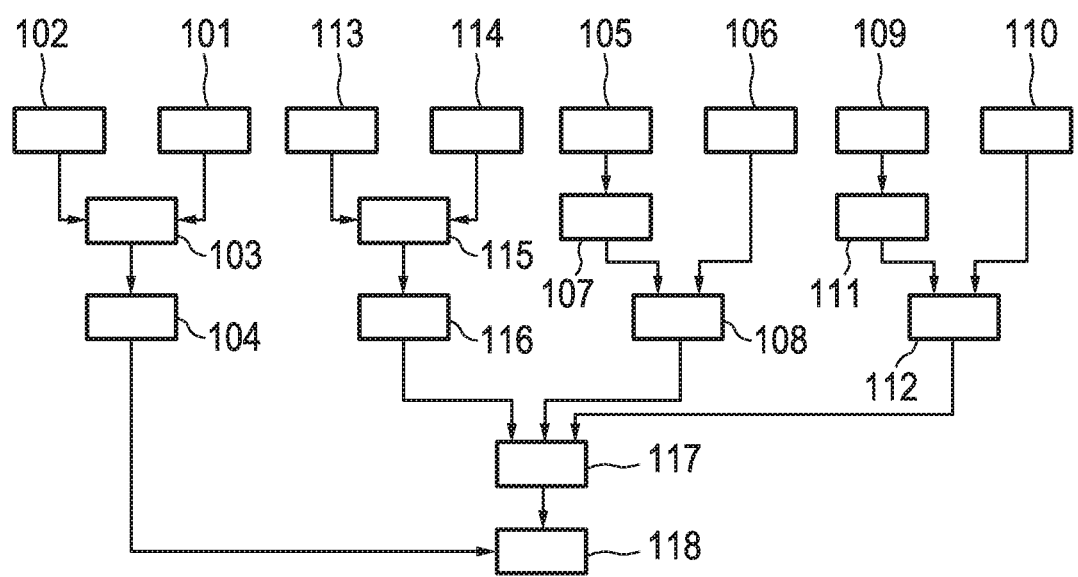
FIG. 4 shows a flowchart exemplarily illustrating an embodiment of a needs determination method for determining needs of a current subject and of current ICGs giving care to the current subject.

In the following an embodiment of a needs determination method will exemplarily be described with reference to a flowchart shown in FIG. 4.

In step 101 a person is allowed to input a current combination of a current subject, current ICGs giving care to the current subject, relationships and optionally also distances between the current subjects and the current ICGs by the graphical user interface 2. The input current combination forms a current pattern describing the "environment" of the current subject, which may be represented by a current graph comprising nodes and edges. In step 102 stored combinations of a stored subject, stored ICGs giving care to the stored subject, relationships and optionally also distances between the stored subject and the stored ICGs are provided by the stored combinations providing unit 3, wherein the stored combinations further include needs assigned to the respective stored subject and the respective stored ICGs of the respective stored combination. The stored combinations form stored patterns describing respective stored subject environments, wherein these stored patterns are preferentially also represented by graphs comprising nodes and edges. In step 103 the combination similarity measure is applied to the current combination and the stored combinations by the similarity unit 4, in order to determine a stored combination which is similar to the current combination. In step 104 needs of the current subject and of the current ICGs of the current combination are determined based on the needs assigned to the stored subject and the ICGs of the determined similar stored combination by the need determination unit 5. In particular, the need determination unit 5 determines the needs assigned to the stored subject and the ICGs of the determined similar stored combination as the needs of the current subject and the current ICGs of the current combination. In this embodiment these determined needs are regarded as being possible needs.

In step 105 an audio recording of a conversation with the current subject and/or the current ICGs is provided by the audio recording providing unit 6 and in step 106 the assignments providing unit 7 provides assignments between a) needs of a subject and/or of ICGs and b) keywords. In step 107 the need determination unit 5 extracts keywords from the provided audio recording and in step 108 the need determination unit 5 determines needs of the current subject and/or of the current ICGs based on the extracted keywords and the provided assignments between a) needs of a subject and/or of ICGs and b) keywords. Also these determined needs are regarded as being possible needs.

In step 109 the subject data set providing unit 8 provides a current subject data set, which comprise subject key data elements, of the current subject of the current combination and the ICG data set providing unit 9 provides a current ICG data set, which comprise ICG key data elements, of a current ICG of the current combination. In step 110 the assignments providing unit 7 provides assignments between a) needs of a subject and b) subject key data elements and assignments between a) needs of an ICG and b) ICG key data elements. In step 111 the need determination unit 5 extracts a subject key data element from the current subject data set and an ICG key data element from the current ICG data set and in step 112 the need determination unit 5 determines a need of the current subject based on the extracted subject key data element and the provided assignments between a) needs of a subject and b) subject key data elements and determines a need of the current ICG based on the extracted ICG key data element and the provided assignments between a) needs of an ICG and b) ICG key data elements. Also these determined needs are regarded as being possible needs.

In step 113 the subject data set providing unit 8 provides a current subject data set of the current subject and the ICG data set providing unit provides a current ICG data set of a current ICG of the current combination, wherein the current subject data set and the current ICG data set provided in step 113 are larger than the current subject data set and the current ICG data set provided in step 109. In particular, in step 113 an entire subject data file and an entire ICG data file may be provided, which may also include doctor notes, whereas in step 109 only a subject profile and an ICG profile may be provided as current data sets, wherein the profiles may only comprise a relatively small number of data like age, gender, and optionally the medical condition. In step 114 the assignments providing unit 7 provides stored subject data sets and assignments between a) needs of a subject and b) the stored subject data sets. Moreover, in step 114 the assignments providing unit 7 provides stored ICG data sets and assignments between a) needs of an ICG and b) the stored ICG data sets. In step 115 the similarity unit 4 applies a subject data similarity measure to the current subject data set and the stored subject data sets, in order to determine a stored subject data set being similar to the current subject data set, and an ICG data similarity measure to the current ICG data set and the stored ICG data sets, in order to determine a stored ICG data set being similar to the current ICG data set. In step 116 the need determination unit 5 determines a need assigned to the similar stored subject data set as a need of the current subject and a need assigned to the similar stored ICG data set as a need of the current ICG. Also these determined needs are regarded as being possible needs.

In step 117 the need determination unit 5 refines the determined possible needs by using the machine learning algorithm. In particular, from the determined set of possible needs are removed and/or further possible needs are added to the set of possible needs, in order to refine the determined set of possible needs. The machine learning algorithm uses as input the determined set of possible needs and provides as output the refined set of needs.

In step 118 the determined possible needs are shown to the person via the graphical user interface 2, wherein the person can confirm or remove the determined possible needs. Moreover, the person can move one or several possible needs from a stakeholder to another stakeholder and confirm the one or several possible needs for the other stakeholder via the graphical user interface 2. Also the directly input needs can be shown in step 118.

The need determination system can support a healthcare provider during the process of identifying the needs, especially the key needs, of both the current subject and his/her current ICGs. It allows the healthcare provider to collect a more complete set of needs in a shorter time frame by offering a tool for extracting needs and for suggesting these needs as possible needs. Since a service blueprint can be created based on the identified needs and since the identified needs are very complete, the created service blueprint can better address the actual needs of the current subject and the current ICGs.

The similarity unit and the need determination unit can be regarded as being a reasoning engine which is adapted to determine needs, especially key needs, based on, for instance, input streams like an audio stream, subject and ICG data and historical patterns describing the environment in which a subject operates. The determined needs are regarded as possible needs which are presented on the graphical user interface, in order to support and guide, for instance, an interaction between the stakeholders. The possible needs can be modified, i.e., for instance, possible needs can be deleted or confirmed, or assigned to another stakeholder and then confirmed, by using the graphical user interface. Also after the possible needs have been determined, the person may be permitted to add further needs directly by using the graphical user interface.

The stored combinations providing unit 3 is preferentially a database in which the stored combinations are stored and from which the stored combinations can be retrieved. However, the stored combinations providing unit 3 can also be a receiving unit for receiving the stored combinations from a database and for providing the received stored combinations. Also the audio recording providing unit 6, the assignments providing unit 7, the subject data set providing unit 8 and the ICG data set providing unit 9 may be databases or receiving units for receiving the respective information from a database and for providing the received information.

The need determination system 1 is preferentially a computer system, wherein all components of the need determination system 1 or some components, especially at least the graphical user interface 2, may be implemented in a tablet computer. The graphical user interface 2 may be adapted to allow the person to input the current subject and the current ICGs by using physical tokens, which can be placed by the person on the tablet computer which can recognize the kind of physical token and the position of the physical token on the graphical user interface 2. Thus, for different stakeholders different physical tokens may be provided, for instance, different physical tokens may be provided for a current subject being a child and a current subject being an adult and different physical tokens may be provided for different current ICGs, for instance, a physical token for a parent, a physical token for a child, a physical token for a spouse, a physical token for a friend, et cetera. The person may place the different physical tokens on the graphical user interface 2 which identifies the kind of physical token at the respective position on the graphical user interface 2, in order to allow the person to input the current subject, the current ICGs, their relationships and also their distances in a relatively simple way. In order to allow the graphical user interface 2 to recognize the respective physical token known techniques can be used like the technique used by Walt Disney's appmates.

The input current subject, current ICGs, relationships and distances form a current pattern, i.e. a current combination, which represents the current subject's environment. This current pattern can be used as one of the inputs to find needs for this environment.

In an embodiment also the distances between current ICGs and/or the relationships between current ICGs can be input for providing a current combination also including distances and/or relationships between current ICGs, wherein also the stored combinations can include distances and/or relationships between ICGs. By using also distances and/or relationships between current ICGs, the determination of the needs of the current ICGs may be further improved.

Moreover, in an embodiment also needs directly input by using the user interface may be assigned to the current combination such that the current combination may also include directly assigned needs of the current subject and/or a current ICG, which may be assigned to respective nodes of a current graph. The determination of the similar stored combination, particularly of the similar stored graph, may then also consider the needs of the current combination. Considering the already input needs, while determining the similar stored combination, may further improve the determination of the needs.

For creating a current pattern, i.e. a current combination, the need determination system, for instance, especially the graphical user interface 2 or the similarity unit 4, may measure the distances between the current subject and the current ICGs on the map shown in FIG. 2. The current pattern may then be defined by the stakeholders, the distances between the current subject and the current ICGs, the given relationships between the current subject and the current ICGs and, if also input via the graphical user interface 2, the input needs of the stakeholders. Such a current pattern can be represented by a current graph comprising a set of nodes representing stakeholders and their needs and a set of edges with distances and relationships. The similarity unit 4 and the need determination unit 5, which may be regarded as being a need extraction engine, may use this current pattern and potentially sub-patterns to identify one or several similar stored patterns via comparing the stakeholders, their distances, their relationships and, if input, their needs.

The need determination system, which can be regarded as comprising a need extraction engine, can provide a set of possible needs for the current subject's environment based on a number of input streams. The subject data set and the ICG data set can be provided by the subject data set and ICG data set providing units by using an electronic health record (EHR) system for providing clinical data, but the subject data set and ICG data set providing units can also comprise or use other sources. For instance, the subject data set and ICG data set providing units can use or comprise a data source in which psychological, social, mental, et cetera data are stored, which can be crucial for determining self-care needs. These data can be located in different data bases or they can be located in a same data base.

In an embodiment the need determination system can also be adapted to receive text input like an email exchange, wherein the assignments providing unit may be adapted to provide assignments between a) needs of a subject and/or needs of an ICG and b) keywords, wherein the need determination unit may be adapted to extract keywords in the received text input and to determine needs, which may be regarded as being possible needs, based on the provided assignments and the extracted keywords.

The combinations, especially the graphs, may also include professional caregivers, wherein to the stored combinations including professional caregivers one or several needs can be assigned, such that, if the current combination also includes a professional caregiver like a nurse, a physician et cetera, also at least one need of the professional caregiver may be determined.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the graphical user interface for allowing a person to input, for instance, a current combination of a current subject, current ICGs, and relationships, the provision of stored combinations, the determination of similarities, the determination of needs, et cetera, performed by one or several units or devices can be performed by any other number of units or devices. These procedures and/or the control of the needs determinations system in accordance with the needs determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a need determination system comprising a user interface for allowing a person to input a current combination of a current subject, at least one current ICG giving care to the current subject, and at least one relationship between the current subject and the at least one current ICG. A combination similarity measure is applied to the current combination and stored combinations, in order to determine a stored combination which is similar to the current combination, wherein a need of the current subject and/or a need of the at least one current ICG are determined based on one or several needs assigned to a stored subject and/or stored ICGs of the determined similar stored combination. This allows for a reliable and fast determination of needs of a subject and/or an ICG with relatively low technical efforts.

The invention claimed is:

1. A need determination system comprising:
   a user interface for inputting a current combination of a current subject, at least one current informal caregiver (ICG) providing informal care to the current subject, and at least one relationship between the current subject and the at least one current ICG, the at least one current ICG having a nonprofessional relationship with the current subject;
   at least one database for storing combinations of a stored subject, at least one stored ICG, and at least one relationship between the stored subject and the at least one stored ICG, and at least one need assigned to the stored subject and at least one need assigned to the at least one stored ICG of the stored combination; a current subject data set of the current subject comprising subject key data elements; assignments between a) needs of a subject and b) subject key data elements; at least one current ICG data set of the at least one current ICG of the current combination, the at least one current ICG data set comprising ICG key data elements; and assignments between a) needs of an ICG and b) ICG key data elements; and
   a computer processor for executing software instructions, stored on a non-transitory medium, to perform steps of:

applying a combination similarity measure to the current combination and the stored combinations in order to determine a stored combination that is similar to the current combination, determining a set of needs comprising at least one need of the current subject based on the at least one need assigned to the stored subject of the determined similar stored combination and at least one need of the at least one current ICG based on the at least one need assigned to the at least one stored ICG of the determined similar stored combination, the at least one need of the at least one current ICG comprising training or information for assisting the at least one current ICG in providing the informal care to the current subject, extracting a subject key data element from the current subject data set and determining a need of the current subject based on the extracted subject key data element and the provided assignments between a) needs of a subject and b) subject key data elements, and extracting an ICG key data element from the at least one current ICG data set and determining a need of the at least one current ICG based on the extracted ICG key data element and the provided assignments between a) needs of an ICG and b) ICG key data elements, and training a machine learning algorithm using the at least one determined need of the current subject and/or the at least one determined need of the at least one current ICG to refine the set of needs.

2. The need determination system of claim 1, wherein refining the set of needs comprises including or excluding one of the at least one determined need of the current subject and/or the at least one determined need of the at least one current ICG.

3. The need determination system as defined in claim 2, wherein the user interface enables a user to confirm or remove a determined need, and wherein the machine learning algorithm is further trained using the confirmed or removed determined need to refine the set of needs.

4. The need determination system as defined in claim 1, wherein the at least one database further stores:
an audio recording of a conversation with the current subject and/or the at least one current ICG,
assignments between a) needs of a subject and/or an ICG and b) keywords,
wherein the computer processor further performs steps of extracting keywords from the audio recording and further determining at least one need of the current subject and/or at least one need of the at least one current ICG based on the extracted keywords and the assignments between a) needs of a subject and/or an ICG and b) keywords.

5. The need determination system as defined in claim 1, wherein the at least one database further stores:
subject data sets and assignments between a) needs of a subject and b) the stored subject data sets,
wherein the computer processor further performs steps of applying a subject data similarity measure to the current subject data set and the stored subject data sets, in order to determine a stored subject data set being similar to the current subject data set, and determining a need assigned to the similar stored subject data set as another need of the current subject.

6. The need determination system as defined in claim 1, wherein the at least one database further stores:

ICG data sets and assignments between a) needs of an ICG and b) the stored ICG data sets,
wherein the computer processor further performs steps of applying an ICG data similarity measure to the at least one current ICG data set and the stored ICG data sets, in order to determine at least one stored ICG data set being similar to the at least one current ICG data set, determining a need assigned to the similar at least one stored ICG data set as another need of the at least one current ICG.

7. The need determination system as defined in claim 1, wherein the at least one database provides the stored combinations as stored graphs, wherein a stored graph comprises nodes, to which the stored subject, the at least one stored ICG and needs are assigned, and at least one edge, which connects the stored subject with the at least one stored ICG and to which the respective at least one relationship between the stored subject and the at least one stored ICG is assigned, wherein the computer processor further performs steps of generating a current graph based on the input current combination and applying the combination similarity measure to the current graph and the stored graph, in order to determine a stored combination which is similar to the current combination.

8. The need determination system as defined in claim 1, wherein the user interface further enables the inputting of the current combination to include at least one distance between the current subject and the at least one current ICG, wherein the stored combinations comprise distances between the respective stored subject and the respective stored at least one ICG.

9. The need determination system as defined in claim 1, wherein the at least one database provides the current combination as a stored combination, while determining at least one need of a subject and at least one need of at least one ICG for a subsequent combination of a subject, at least one ICG and at least one relationship between the subject and the at least one ICG which will be input via the user interface.

10. The need determination system as defined in claim 1, wherein the user interface further enables a) inputting a need and assigning the input need to the current subject or the at least one current ICG and/or b) confirming or removing a determined need.

11. A needs determination method comprising:
enabling a user to input a current combination of a current subject, at least one current informal caregiver (ICG) providing informal care to the current subject, and at least one relationship between the current subject and the at least one current ICG using a graphical user interface, the at least one current ICG having a non-professional relationship with the current subject;
providing stored combinations comprising a stored subject, at least one stored ICG giving care to the stored subject, at least one relationship between the stored subject and the at least one stored ICG, and at least one need assigned to the stored subject and at least one need assigned to the respective at least one stored ICG of the respective stored combination;
providing stored current subject data set of the current subject comprising subject key data elements, assignments between a) needs of a subject and b) subject key data elements, at least one current ICG data set of the at least one current ICG of the current combination, the at least one current ICG data set comprising ICG key data elements, and assignments between a) needs of an ICG and b) ICG key data elements;

applying a combination similarity measure to the current combination and the stored combinations in order to determine a stored combination that is similar to the current combination;

determining a set of needs comprising at least one need of the current subject based on the at least one need assigned to the stored subject of the determined similar stored combination and at least one need of the at least one current ICG based on the at least one need assigned to the at least one stored ICG of the determined similar stored combination, the at least one need of the at least one current ICG comprising training or information for assisting the at least one current ICG in providing the informal care to the current subject;

extracting a subject key data elements from the current subject data set and determining a need of the current subject based on the extracted subject key data element and the provided assignments between a) needs of a subject and b) subject key data elements;

extracting an ICG key data element from the at least one current ICG data set and determining a need of the at least one current ICG based on the extracted ICG key data element and the provided assignments between a) needs of an ICG and b) ICG key data elements; and training a machine learning algorithm using the at least one determined need of the current subject and/or the at least one determined need of the at least one current ICG to refine the set of needs.

12. The method of claim 11, further comprising:
enabling the user to provide an input confirming or removing a determined need, wherein the machine learning algorithm is further trained using the confirmed or removed determined need.

13. The method of claim 11, further comprising:
storing an audio recording of a conversation with the current subject and/or the at least one current ICG; and
extracting keywords from the audio recording and determining at least one need of the current subject and/or at least one need of the at least one current ICG based on the extracted keywords.

14. The method of claim 11, further comprising:
enabling the user interface to input the current combination to include at least one distance between the current subject and the at least one current ICG, wherein the stored combinations comprise distances between the respective stored subject and the respective stored at least one ICG.

15. A need determination system comprising:
a user interface for inputting a current combination of a current subject, at least one current informal caregiver (ICG) providing informal care to the current subject, and at least one relationship between the current subject and the at least one current ICG, the at least one current ICG having a nonprofessional relationship with the current subject;
at least one database for storing combinations of a stored subject, at least one stored ICG, and at least one relationship between the stored subject and the at least one stored ICG, and at least one need assigned to the stored subject and at least one need assigned to the at least one stored ICG of the stored combination; a current subject data set of the current subject; subject data sets and assignments between a) needs of a subject and b) the stored subject data sets; at least one current ICG data set of the at least one current ICG of the current combination; and ICG data sets and assignments between a) needs of an ICG and b) the stored ICG data sets; and
a computer processor for executing software instructions, stored on a non-transitory medium, to perform steps of:
applying a combination similarity measure to the current combination and the stored combinations in order to determine a stored combination that is similar to the current combination,
determining a set of needs comprising at least one need of the current subject based on the at least one need assigned to the stored subject of the determined similar stored combination and at least one need of the at least one current ICG based on the at least one need assigned to the at least one stored ICG of the determined similar stored combination, the at least one need of the at least one current ICG comprising training or information for assisting the at least one current ICG in providing the informal care to the current subject,
applying a subject data similarity measure to the current subject data set and the stored subject data sets in order to determine a stored subject data set being similar to the current subject data set, and determining a need assigned to the similar stored subject data set as a need of the current subject,
applying an ICG data similarity measure to the at least one current ICG data set and the stored ICG data sets in order to determine at least one stored ICG data set being similar to the at least one current ICG data set, and determining a need assigned to the similar at least one stored ICG data set as a need of the at least one current ICG, the at least one need of the at least one current ICG comprising training or information for assisting the at least one current ICG in providing the informal care to the current subject, and
training a machine learning algorithm using the at least one determined need of the current subject and/or the at least one determined need of the at least one current ICG to refine the set of needs.

16. The need determination system as defined in claim 15, wherein the at least one database further stores:
subject key data elements included in the current subject data set of the current subject, and
assignments between a) needs of a subject and b) subject key data elements,
wherein the computer processor further performs steps of extracting a subject key data element from the current subject data set and determining another need of the current subject based on the extracted subject key data element and the provided assignments between a) needs of a subject and b) subject key data elements.

17. The need determination system as defined in claim 15, wherein the at least one database further stores:
ICG key data elements included in the at least one current ICG data set, and
assignments between a) needs of an ICG and b) ICG key data elements,
wherein the computer processor further performs steps of extracting an ICG key data element from the at least one current ICG data set and determining another need of the at least one current ICG based on the extracted ICG key data element and the provided assignments between a) needs of an ICG and b) ICG key data elements.

* * * * *